United States Patent [19]

McBeath et al.

[11] Patent Number: 5,218,481
[45] Date of Patent: Jun. 8, 1993

[54] OPTICAL INSPECTION APPARATUS

[75] Inventors: John McBeath, Nelson; Graham Smith, Crosshills, Near Keighley, both of United Kingdom

[73] Assignee: Laroy Optical Limited, North Yorkshire, United Kingdom

[21] Appl. No.: 698,083

[22] Filed: May 10, 1991

[51] Int. Cl.⁵ ............................................. G02B 27/02
[52] U.S. Cl. .................................. 359/802; 359/800; 356/391
[58] Field of Search ............... 359/798, 799, 800, 801, 359/802, 804, 810, 649, 651, 656, 661, 672, 368, 479, 888, 366, 369; 250/492.2; 355/53, 57; 353/98; 356/376, 383, 384, 390, 391

[56] References Cited

U.S. PATENT DOCUMENTS

| | | | |
|---|---|---|---|
| 2,552,238 | 5/1951 | Turner et al. | |
| 2,552,272 | 5/1951 | Fultz. | |
| 2,776,696 | 1/1957 | Meier | 356/390 |
| 3,539,798 | 11/1970 | Perry | 359/799 |
| 3,917,391 | 11/1975 | Padula et al. | 356/391 |

FOREIGN PATENT DOCUMENTS 555989 7/1932 Fed. Rep. of Germany.
2107899 5/1983 United Kingdom.

Primary Examiner—Loha Ben
Attorney, Agent, or Firm—Shoemaker and Mattare

[57] ABSTRACT

An optical projection system for projecting a magnified image of an object includes a 1:2 relay lens having a magnification of ×0.5. The object is illuminated by a collimated substantially parallel light beam from a source and the 1:2 relay lens produces an intermediate shadow image at its focal plane. A projection lens is located to project a magnified final image of the intermediate image on the screen. While it is preferred that the relay lens has a magnification of ×0.5, the relay lens may have a different magnification less than ×1.

4 Claims, 1 Drawing Sheet

OPTICAL INSPECTION APPARATUS

BACKGROUND OF THE INVENTION

This invention relates to optical inspection apparatus in which a magnified image of an object is projected on a screen to enable inspection of the object.

FIELD OF THE INVENTION

In known optical inspection apparatus, a projection lens produces a magnified image on a screen of an illuminated object. A number of different projection lenses may be provided, for example mounted on a turret, each having a different magnification. A user of the inspection system may then select the required magnification by selection of an appropriate projection lens. A 1:1 relay lens having a magnification of ×1 is provided between the object and the projection lens to enable the optical system to be spaced at a constant distance from the object being inspected regardless of the magnification produced by the projection lens. Light from a source is collimated into a near parallel beam to illuminate the profile of an object to be viewed. The 1:1 relay lens produces a shadow image of the object at the plane of the relay lens and this shadow image is then magnified by a projection lens to produce a magnified image on a screen of the object. The shadow image produced at the focal plane of the relay lens has the same dimensions as those of the object and accordingly the projection lens is required to have a optical diameter sufficient to accommodate a shadow image of these dimensions.

SUMMARY OF THE INVENTION

According to the invention optical inspection apparatus for producing a projected image of an object comprises a first lens having a magnification less than ×1 to produce an intermediate image of an object, the intermediate image being of reduced dimensions relative to the dimensions of the object and a second lens device to produce a projected magnified final image of the intermediate image.

BRIEF DESCRIPTION OF THE DRAWINGS

An embodiment of the invention will now be described by way of example with reference to the drawings in which.

DETAILED DESCRIPTION OF THE INVENTION

Figure 1:
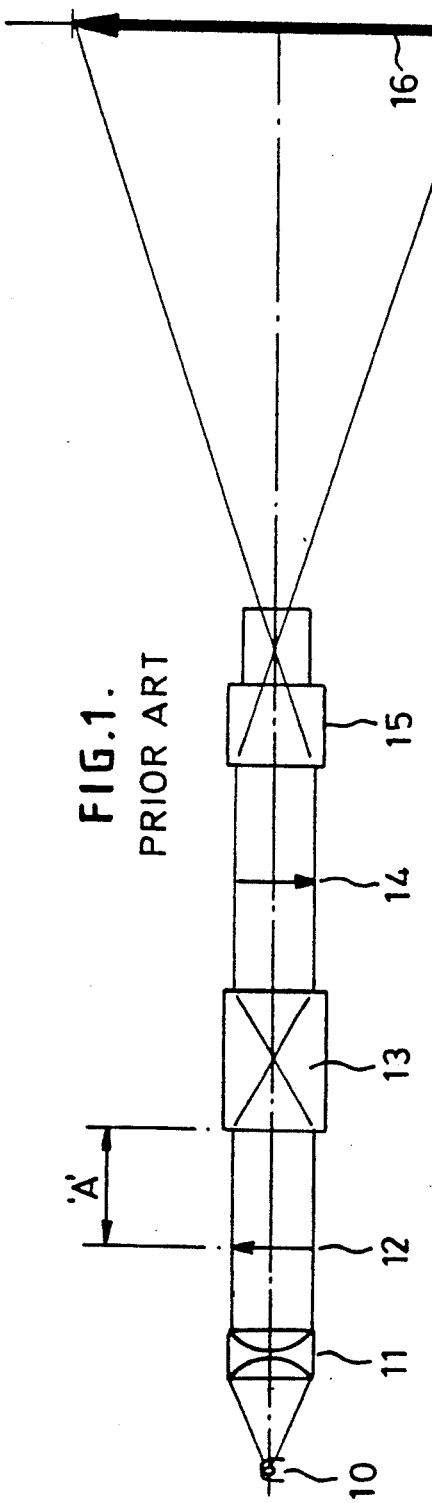
FIG. 1 is a diagram illustrating a prior art projection system.

Referring first to FIG. 1, a known optical projection system for an inspection apparatus used for inspecting the profile of an object comprises a source 10 of light and a condenser lens 11 for collimating the light from the source 10 into a substantially parallel beam of light. An object 12 to be inspected is located in the path of the parallel beam of light and a 1:1 relay lens 13 spaced at a distance 'A' from the object produces, at the focal plane of the lens 13, a shadow image 14 of the profile of the object 12. The relay lens has a magnification of ×1 and hence the shadow image 14 is of the same dimensions as the object 12. A projection lens 15 is located to magnify the shadow image and to project a magnified final image 16 on a viewing screen 17. The magnification of the projection lens 15 is chosen to provide the required degree of magnification of the final image 16 as compared with the object 12 and for example may be ×10 to produce a final image 16 ten times the size of the object 12. It will be appreciated that since the relay lens has a magnification of ×1 and the shadow image 14 is of the same dimensions as the object 12, the optical aperture of the relay lens must be sufficiently large to accommodate these dimensions of object and image and in addition the projection lens 15 is required to have an optical aperture sufficiently large to accommodate the dimensions of the intermediate shadow image 14.

Figure 2:
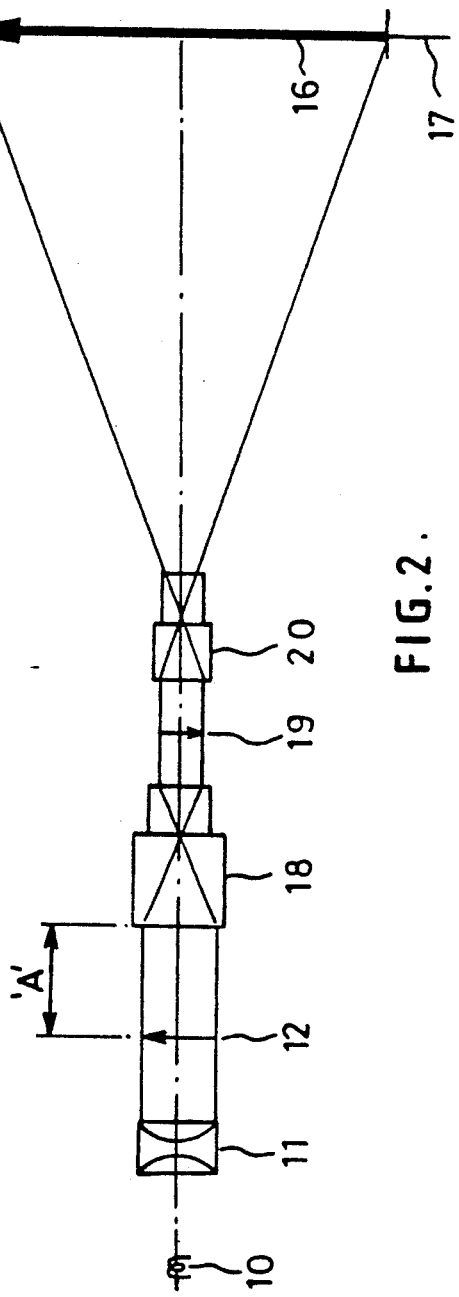
FIG. 2 is a diagram illustrating a projection system in accordance with the invention.

In the optical projection system in accordance with the invention and illustrated in FIG. 2, the relay lens 13 of the prior art system having a magnification of 1 is replaced by a 1:2 relay lens 18 having a magnification of ×0.5. The object 12 is illuminated by a collimated substantially parallel light beam from a source 10 and the 1:2 relay lens 18 produces an intermediate shadow image 19 at its focal plane. Since the 1:2 relay lens has a magnification of ×0.5, the intermediate shadow image 19 is half the size of the object 12. The 1:2 relay lens 18 is designed and constructed to provide optimum optical performance when producing this half size image of the object. A projection lens 20 is located to project a magnified final image 16 of the intermediate image 19 on the screen 17. While it is preferred that the relay lens 18 has a magnification of ×0.5, the relay lens may have a different magnification. In order to produce a required magnification of the final image 16 in relation to the object 12, the magnification of the projection lens 20 as compared with the projection lens 15 is increased in proportion to the magnification of the relay lens in accordance with the formula:

magnification of final image = (magnification of relay lens) × (magnification of projection lens)

Accordingly if, for example, a magnification of ×10 is required for the final image 16 and using a 1:2 relay lens having a magnification of ×0.5 the projection lens would be required to have a magnification of ×20.

Since the intermediate image 19 is of reduced size when using a relay lens 18 having a magnification less than ×1 the projection lens 20 can have a smaller optical diameter than that of the projection lens required when using a 1:1 relay lens having ×1 magnification. The cost of lenses is in proportion to the area of the lens and hence considerable saving in the cost of the projection lens is obtained by the use of a relay lens having a magnification less than ×1 particularly when a number of projection lenses are provided to enable different magnifications to be obtained. The reduction in size of the projection lenses enables the size and complexity of the turret supporting the lenses to reduced. The constant working distance 'A' between the object 12 and the relay lens 18 is retained and may be of the same dimension as in the prior art system using a 1:1 relay lens. A further advantage obtained by the use of a relay lens of magnification less than ×1 is that the overall length of the optical system is reduced thereby enabling a more compact and less expensive construction of the inspection apparatus.

Usually it is desirable to provide for a number of different magnifications of the final image which may be selected by a user of the inspection equipment. For this reason a number of projection lenses having different magnifications are mounted on a turret which may be rotated by the user to bring any selected one of the projection lenses into an operative position. Alternatively, the lenses may be mounted on a multi-position slide to enable any selected one of the lenses to be moved into an operative position.

While the optical system has been described in relation to an object illuminated from the rear, the intermediate and final images may be produced from direct (episcopic) illumination of the object.

We claim:

1. Optical inspection apparatus for producing a projected image of an object comprising a first lens structure having a magnification less than ×1 to produce an intermediate image of said object, said intermediate image being of reduced dimensions relative to the dimensions of the object and a second lens structure to produce a projected magnified final image of the intermediate image.

2. Optical inspection apparatus as claimed in claim 1 wherein said first lens structure has a magnification of ×0.5.

3. Optical inspection apparatus as claimed in claim 1 wherein the second lens structure has an optical diameter corresponding to less than the dimensions of the object being viewed and corresponding to the dimensions of the intermediate image.

4. Optical inspection apparatus for producing a projected image of an object comprising a source of light for illumination of said object with a collimated beam of light of substantially parallel rays; first lens means having a magnification less than ×1 to produce an intermediate shadow image of said object, said shadow image having dimensions less than corresponding dimensions of said object; and second lens means to produce a projected magnified image of said shadow image.

* * * * *